United States Patent
Ohtani et al.

(10) Patent No.: US 11,614,858 B2
(45) Date of Patent: Mar. 28, 2023

(54) MEDICAL IMAGE DIAGNOSTIC APPARATUS

(71) Applicant: Shimadzu Corporation, Kyoto (JP)

(72) Inventors: Atsushi Ohtani, Kyoto (JP); Natsuno Ommori, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/597,873

(22) Filed: Oct. 10, 2019

(65) Prior Publication Data

US 2020/0142553 A1    May 7, 2020

(30) Foreign Application Priority Data

Nov. 6, 2018 (JP) .............................. JP2018-208678

(51) Int. Cl.
  *G06F 3/04847*  (2022.01)
  *G06F 3/0483*  (2013.01)
  (Continued)

(52) U.S. Cl.
  CPC ........ *G06F 3/04847* (2013.01); *G06F 3/0482* (2013.01); *G06F 3/0483* (2013.01);
  (Continued)

(58) Field of Classification Search
  CPC ............. G06F 3/04847; G06F 3/04886; G06F 3/0483; G06F 3/0482; G06F 2203/04803; G16H 30/40; G06T 11/003; G06T 2211/40
  See application file for complete search history.

(56) References Cited

U.S. PATENT DOCUMENTS

| | | |
|---|---|---|
| 7,900,146 B2 | 3/2011 | Kozuka et al. |
| 2003/0095150 A1 | 5/2003 | Trevino et al. |
| | (Continued) | |

FOREIGN PATENT DOCUMENTS

| | | |
|---|---|---|
| JP | 2003210433 A | 7/2003 |
| JP | 2006-309353 A | 11/2006 |
| JP | 2013-185855 A | 9/2013 |

OTHER PUBLICATIONS

Notice of Reasons for Refusal, dated Nov. 19, 2021, from the Japanese Patent Office, for corresponding Japanese Patent Application No. 2018-208678, and English-language translation thereof (.
(Continued)

*Primary Examiner* — Roberto Borja
(74) *Attorney, Agent, or Firm* — Muir Patent Law, PLLC (57) ABSTRACT

The medical image diagnostic apparatus is configured to generate a medical image based on data collected from a subject when an operator sequentially performs a plurality of steps. A display unit has a display screen. An operation unit receives an operation of an operator on the display screen. A control unit controls the display unit based on the operation received by the operation unit. The display unit displays a plurality of setting screens respectively corresponding to the plurality of steps on a display screen in a superimposed manner. The control unit is configured to switch the setting screen of the uppermost layer between the plurality of setting screens based on the operation received by the operation unit. The display unit further displays, in each of the plurality of setting screens, a plurality of wizard screens for sequentially inputting a plurality of pieces of information in a wizard format.

7 Claims, 8 Drawing Sheets

(51) Int. Cl.
   *G06F 3/04886*  (2022.01)
   *G06F 3/0482*  (2013.01)
   *G16H 30/40*  (2018.01)
   *G06T 11/00*  (2006.01)

(52) U.S. Cl.
   CPC ........ *G06F 3/04886* (2013.01); *G06T 11/003* (2013.01); *G16H 30/40* (2018.01); *G06F 2203/04803* (2013.01); *G06T 2211/40* (2013.01)

(56) References Cited

U.S. PATENT DOCUMENTS

| | | | |
|---|---|---|---|
| 2006/0239708 A1 | 10/2006 | Kozuka et al. | |
| 2007/0162159 A1* | 7/2007 | Ladenburger | G06F 19/325 700/17 |
| 2008/0317206 A1* | 12/2008 | Yoshino | G16H 80/00 378/98 |
| 2011/0093779 A1* | 4/2011 | Gador | G06F 9/453 715/705 |
| 2014/0098932 A1* | 4/2014 | Profio | G16H 40/63 378/19 |
| 2019/0365350 A1* | 12/2019 | Chiang | A61B 8/4427 |

OTHER PUBLICATIONS

Office Action, dated Jun. 1, 2022, dated Jun. 7, 2022, from the Japanese Patent Office for corresponding Japanese Patent Application No. 2018-208678. along with English-language machine translation of the same (4 pages).

\* cited by examiner

| | Inspection selection | Imaging | Completion | 42 |

40A — Info setting

Select inspection

| Name | Inspection site |
|---|---|
| Shimadzu Hanako | mammo |
| Jane Smith | mammo |

| | |
|---|---|
| Name | Jane Smith |
| ID | 213546 |
| Gender | Female |
| Date of birth | 1996/07/30 |
| Age | 22 |
| Injection Time | 2018/09/01 12:00:00 |
| Elapsed Time | 01:14:22 |

40B — Inspection

40C — Image transmission

Cancel    Next ▶

(b)

| Inspection selection | Imaging | Completion | 42 |

40A — Info setting

Select series and start scanning

| Series | Position | Step | Acq Time | Comment |
|---|---|---|---|---|
| 01 | mammo,R | Step1 | 0 | |
| | | Step2 | 0 | |
| 02 | mammo,L | | 0 | |

Preview

40B — Inspection

Remaining time :    :    Count rate

ACQ Start

40C — Image transmission

Cancel    ◀ Back   Next ▶

MEDICAL IMAGE DIAGNOSTIC APPARATUS

CROSS-REFERENCE TO RELATED APPLICATIONS

The present application claims priority under 35 U.S.C. 119 to Japanese Patent Application No. 2018-208678 filed on Nov. 6, 2018, the entire disclosure of which is incorporated by reference in its entirety.

TECHNICAL FIELD

The present invention relates to a medical image diagnostic apparatus.

BACKGROUND ART

A medical image diagnostic apparatus is configured to generate a medical image based on data collected from a subject. As a medical image diagnostic apparatus, there is a nuclear medicine diagnostic apparatus configured to image distribution of radiopharmaceuticals emitted from a subject. As a nuclear medicine diagnostic apparatus, Japanese Patent Application Publication No. 2013-185855 (Patent Document 1) discloses a PET (Positron Emission Tomography) apparatus.

A PET apparatus is configured to detect radiation generated resulting from annihilation of a positron by a plurality of detectors arranged in an annular shape. Based on a pair of radiation (annihilation radiation pair) simultaneously detected by a plurality of detectors, a tomographic image of a subject is reconstructed.

PRIOR ART

Patent Document

Patent Document 1: Japanese Unexamined Patent Application Publication No. 2013-185855

SUMMARY OF THE INVENTION

Problems to be Solved by the Invention

In the PET apparatus described above, various biological functions can be quantitatively measured by measuring the process of drug accumulations in a target tissue over time after administering radioactive pharmaceuticals to a subject. On the other hand, the operator of the PET apparatus is required to perform setting of various information for each subject. The information to be set includes information, such as, e.g., the body weight of the subject and the medication information immediately before the inspection, which cannot be confirmed until immediately before the inspection. Therefore, the operator is required to set a lot of information immediately before the inspection, so that there is a concern that it takes time and effort.

A relatively long time is required to reconstruct a tomographic image from the collected data. As a result, since it takes a considerable amount of time to generate tomographic images of a plurality of subjects, the operator is attempting to improve the work efficiency by performing generation processing of tomographic images of the plurality of subjects in parallel.

However, in a conventional PET apparatus, for example, in cases where, during a step of reconstructing a tomographic image for one subject, in the case of performing a step of setting an inspection condition for another subject, there is a case in which the setting screen of another subject's inspection condition is displayed on a display screen in a state in which a tomographic image is displayed on the display screen of a display unit. At this time, if important information such as a tomographic image becomes unable to be seen, it is troublesome. Therefore, the apparatus is configured such that the operation can be performed in a state in which the setting screen of the inspection condition is displayed while securing the display region of the tomographic image. Therefore, there is a concern that the size of the display region for displaying each step may be reduced and the transition of the screen may become complicated. Further, as the screen becomes complicated, there is a concern that the operator may input erroneous information or may make an erroneous operation such as omission of an information input.

The present invention has been made to solve the aforementioned problems, and the object thereof is to provide a medical image diagnostic apparatus that enables an operator to efficiently operate with a simple operation.

Means for Solving the Problems

According to one aspect of the present invention, a medical image diagnostic apparatus is configured to generate a medical image based on data collected from a subject when an operator sequentially performs a plurality of steps. The medical image diagnostic apparatus includes a display unit including a display screen, an operation unit configured to receive an operation of the operator to the display screen, and a control unit configured to control the display unit based on the operation received by the operation unit. The display unit is configured to display a plurality of setting screens respectively corresponding to the plurality of steps on the display screen in a superimposed manner. The control unit is configured to switch the setting screen of an uppermost layer between the plurality of setting screens based on the operation received by the operation unit. The display unit is further configured to display, in each of the plurality of setting screens, a plurality of wizard screens for sequentially inputting a plurality of pieces of information in a wizard format.

According to the above-described medical image diagnostic apparatus, when generating medical images of a plurality of subjects, while performing a step for a subject, when another step for another subject is performed, the operator can execute these two steps in parallel by switching the setting screen of the uppermost layer of the display screen. With this, when the setting screen of one step is being displayed in the display unit, since the setting screen of another step is in a non-displayed state, it becomes clear to the operator which step is currently being performed. Further, compared with the mode in which the two setting screens respectively corresponding to the two steps are displayed side by side on the display screen, the respective setting screens can be prevented from being miniaturized and complicated. Therefore, it is possible to reduce the possibility that the operator performs erroneous operations.

Further, since the setting screen of each step is configured to display a plurality of wizard screens for sequentially inputting a plurality of pieces of information set in the corresponding step in the wizard format, the number of objects to be displayed on each setting screen can be reduced. This can simplify the setting screen and improve the operability. Further, since the operator can set a plurality of pieces of information by performing the operation in the interactive format, the setting of the plurality of pieces of information can be simplified.

Preferably, the display unit is further configured to display a plurality of objects for receiving an operation that the operation unit switches the setting screen of an uppermost layer, corresponding to the plurality of setting screens.

According to this, the operator can switch the setting screen of the uppermost layer of the display screen by performing an operation of selecting one object between a plurality of objects.

Preferably, the control unit switches the setting screen of the uppermost layer in a state in which the wizard screen displayed on the setting screen of the uppermost layer is held when the operation unit received the operation.

According to this, in the case of performing a plurality of steps in parallel, the setting screen of the uppermost layer can be switched between a plurality of setting screens while retaining the information input for the setting screen in each step. Therefore, when the setting screen of the uppermost layer is switched, it is possible to avoid duplication of effort that information is set from the beginning in the setting screen after the switching. As a result, the work efficiency in the process of generating medical images of a plurality of subjects can be improved.

Preferably, the plurality of setting screens includes a first setting screen for setting information on the subject, a second setting screen for setting information on collection of the data and generation of the medical image, and a third setting screen for setting information regarding storage of the medical image. The display unit is configured to display the plurality of wizard screens in each of the first to third setting screens. The control unit switches the setting screen of the uppermost layer between the first to third setting screens based on the operation received by the operation unit and switches the setting screen of the uppermost layer in a state in which the wizard screen displayed on the setting screen of the uppermost layer is held when the operation unit received the operation.

According to this, in the process of generating medical images of a plurality of subjects, the operator can work efficiently with a simple operation.

Preferably, the display screen of the display unit includes a first display region for displaying the setting screen of the uppermost layer, and a second display region arranged side by side with the first display region and configured to display status information of the medical image diagnostic apparatus.

Preferably, the status information includes at least one of information on a progress of the plurality of steps and information on an operating status of the medical image diagnostic apparatus.

According to this, the operator can always confirm the progress status of the inspection and the status of the medical image diagnostic apparatus when setting the information on the setting screen.

Preferably, the display screen of the display unit further includes a third display region for displaying a message to the operator.

According to this, when setting information on the setting screen, even if a message, such as, e.g., an error message and a warning message, occurs, the message is displayed in the display region other than the setting screen, so the setting screen is not disturbed.

Preferably, the first display region displays, together with the wizard screen, the progress of the step corresponding to the setting screen of the uppermost layer.

According to this, the operator can easily confirm the progress in each step.

According to another aspect of the present invention, a medical image diagnostic apparatus is configured to generate a medical image based on data collected from a subject when an operator sequentially performs a plurality of steps. The medical image diagnostic apparatus includes a display unit including a display screen, and an operation unit configured to receive an operation of the operator to the display screen. The display unit includes a plurality of setting screens corresponding to the plurality of steps, and is configured to display a first setting screen between the plurality of setting screens on the display screen based on the operation received by the operation unit. The display unit is further configured to display a plurality of objects that the operation unit receives an operation of selecting the first setting screen, corresponding to the plurality of setting screens, and a plurality of wizard screens for sequentially inputting a plurality of pieces of information in a wizard format, in each of the plurality of setting screens.

Effects of the Invention

According to the present invention, it is possible to provide a medical image diagnostic apparatus that enables an operator to efficiently operate with simple operations.

EMBODIMENTS FOR CARRYING OUT THE INVENTION

Hereinafter, some embodiments of the present invention will be described with reference to the attached figures. In the following description, note that the same or corresponding portion in the figures is allotted by the same reference symbol, and the description thereof will not be repeated in principle.

Figure 1:
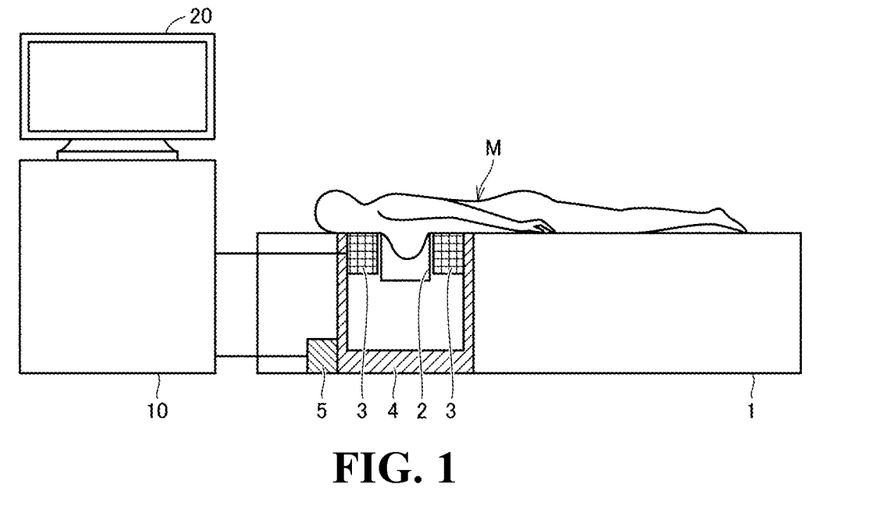
FIG. 1 is a side view of a medical image diagnostic apparatus according to an embodiment of the present invention.

FIG. 1 is a side view of a medical image diagnostic apparatus according to an embodiment of the present invention. The medical image diagnostic apparatus according to this embodiment is configured to generate a medical image based on data collected from a subject M. In the following description, a nuclear medicine diagnostic apparatus is exemplified as a medical image diagnostic apparatus. In the example of FIG. 1, the nuclear medicine diagnostic appliance is a PET (Positron Emission Tomography) apparatus.

Referring to FIG. 1, the PET apparatus 100 is applied to a mammogram for detecting breast cancer of a subject M. The PET apparatus 100 is provided with a gantry 1 for placing a subject M in a prone posture. In the placement surface of the gantry 1, an opening portion 2 for inserting a breast is formed to diagnose the breast below the placement surface.

In the gantry 1, a PET detector 3, a support portion 4, and a drive unit 5 are installed. The PET detector 3 detects γ-rays generated from the subject M. The support portion 4 supports the PET detector 3. The drive unit 5 moves the column portion of the support portion 4 in the up-down direction, and reciprocates along the horizontal plane.

The PET detector 3 includes a plurality of γ-ray detector groups. The plurality of γ-ray detector groups is arranged in a circle along the placement surface of the gantry 1. In this embodiment, the support surface is a horizontal plane, and the plurality of γ-ray detector groups is arranged in a circle along the horizontal plane that is the support surface. The plurality of γ-ray detector groups is arranged so as to surround the breast inserted in the opening portion 2.

In the PET detector 3, the γ-ray detector group has a scintillator block, a light guide, and a photomultiplier tube (all not shown). The scintillator block consists of a plurality of scintillators. The scintillator block converts γ-rays generated from the subject M to which a radioactive pharmaceutical has been administered into light. The light guide guides the converted light. The photomultiplier tube photoelectrically converts the guided light and outputs an electric signal.

The column portion of the support portion 4 is configured to move in a vertical direction with respect to the support surface. By moving in this manner, the PET detector 3 supported by the support portion 4 can be moved in the vertical direction with respect to the rotation surface of the support surface. The drive unit 5 moves the column portion of the support portion in the up-down direction perpendicular to the horizontal plane which is the support surface.

The support portion 4 is configured to move, in addition to in a vertical direction with respect to the horizontal plane which is the support surface as described above, along the support surface. With this, it is possible to move the PET detector 3 in the gantry 1 along the support surface. In this embodiment, the drive unit 5 can reciprocate the PET detector 3 along the horizontal plane by reciprocating the support portion 4 along the horizontal plane.

The drive unit 5 is composed of, for example, a motor, a drive shaft, a pinion, a rack, and a guide rail (none of which are shown). The drive unit 5 rotates the pinion via the drive shaft by driving the motor to move the rack fitted to the pinion up and down along the guide rail. As the guide rail moves up and down, the support portion 4 is moved up and down electrically. Also, a rail (not shown) is laid along the floor below the opening portion 2, and wheels, etc., provided at the bottom of the base portion of the support portion 4 are moved on the rail, whereby the support portion 4 is moved forward and backward along the horizontal plane.

Figure 2:
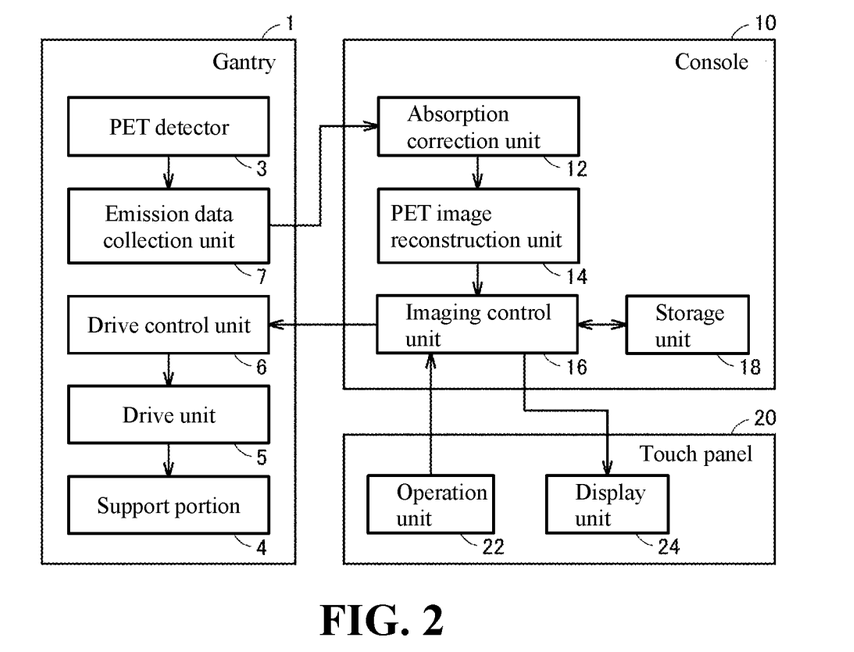
FIG. 2 is a block diagram of a PET apparatus shown in FIG. 1.

FIG. 2 is a block diagram of the PET apparatus 100 shown in FIG. 1. Referring to FIG. 2, the PET apparatus 100 is provided with a gantry 1, a console 10, and a touch panel 20. The gantry 1 is provided with, in addition to the PET detector 3, the support portion 4, and the drive unit 5 described above, a drive control unit 6 and an emission data collection unit 7. The console 10 is provided with an absorption correction unit 12, a PET image reconstruction unit 14, an imaging control unit 16, and a storage unit 18.

The drive control unit 6 controls the drive portion (for example, a motor) of the drive unit 5 and, outputs a braking command to the drive portion when the timing of the movement end is received based on a position detection sensor (not shown) provided to the support portion 4. The drive control unit 6 also outputs a data collection command to the imaging control unit 16. The drive control unit 6 and the imaging control unit 16 are each configured by a central processing unit (CPU: Central Processing Unit) or the like. The position detection sensor may be a non-contact sensor represented by a photo sensor or the like, or may be a contact sensor represented by a micro-switch or the like.

The emission data collection unit 7 collects emission data which is nuclear medicine data based on γ-rays detected by the PET detector 3. The emission data collection unit 7 includes a coincidence counting circuit. The collected emission data is output to the absorption correction unit 12 in the console 10.

The absorption correction unit 12 performs an absorption correction of the emission data. Specifically, the absorption correction unit 12 derives correction data in which the γ-ray absorption coefficient distribution of the breast of the subject M is considered, and makes the correction data act on the emission data. The emission data subjected to the absorption correction is output to the PET image reconstruction unit 14.

The PET image reconstruction unit 14 reconstructs a PET image with the emission data subjected to the absorption correction as projection data. The tomographic image in which the operator has specified a region may be reconstructed as a PET image. Alternatively, the PET image reconstruction unit 14 may reconstruct 3D data and then generate a tomographic image. These image data are displayed on the display unit 24 of the touch panel 20 and stored in the storage unit 18. The absorption correction unit 12 and the PET image reconstruction unit 14 may be each configured by a microprocessor or a FPGA (Field Programmable Gate Array), or may be a part of the CPU of the imaging control unit 16.

The imaging control unit 16 collectively controls each portion constituting the PET apparatus 100. Specifically, the imaging control unit 16 controls the drive performed by the drive unit 5 via the drive control unit 6. When the drive control unit 6 receives the timing of movement end based on the position detection sensor provided to the support portion 4, the imaging control unit 16 receives the data collection command output from the drive control unit 6 and outputs each data collection command to the emission data collection unit 7 and the absorption correction unit 12.

The imaging control unit 16 also outputs a projection data reconstruction command to the PET image reconstruction unit 14. The imaging control unit 16 is further configured to control the display unit 24 based on the operation received by the operation unit 22 of the touch panel 20. The imaging control unit 16 corresponds to an example of the "control unit".

The touch panel 20 is provided with an operation unit 22 for receiving an operation of an operator and a display unit 24 for displaying information. The display unit 24 is provided with a display screen configured by an LCD (liquid crystal display) panel, an organic EL (electroluminescence), a CRT, and the like. The operation unit 22 is provided integrally with the display screen to configure a touch panel. The operation unit 22 receives a touch operation of an operator on the touch panel 20. The operation unit 22 includes objects such as an input key, etc., for inputting characters and numerical values to a GUI (Graphical User Interface) configuring the setting screen.

The operation unit 22 outputs data and commands input by the operator to the imaging control unit 16. The operator also inputs, e.g., a region designation of a tomogram to the operation unit 22. The operation unit 22 may be configured by, in addition to the touch panel described above, a pointing device, such as, e.g., a mouse, a keyboard, a joystick, and a trackball.

The storage unit 18 is storing various image data and the like, and is configured by a flash memory, a hard disk, a storage, and the like.

Next, the flow of generation processing of a medical image in the medical image diagnostic apparatus according to this embodiment will be described. In the following description, generation processing of a PET image in the PET apparatus 100 shown in FIG. 1 is exemplified.

Figure 3:
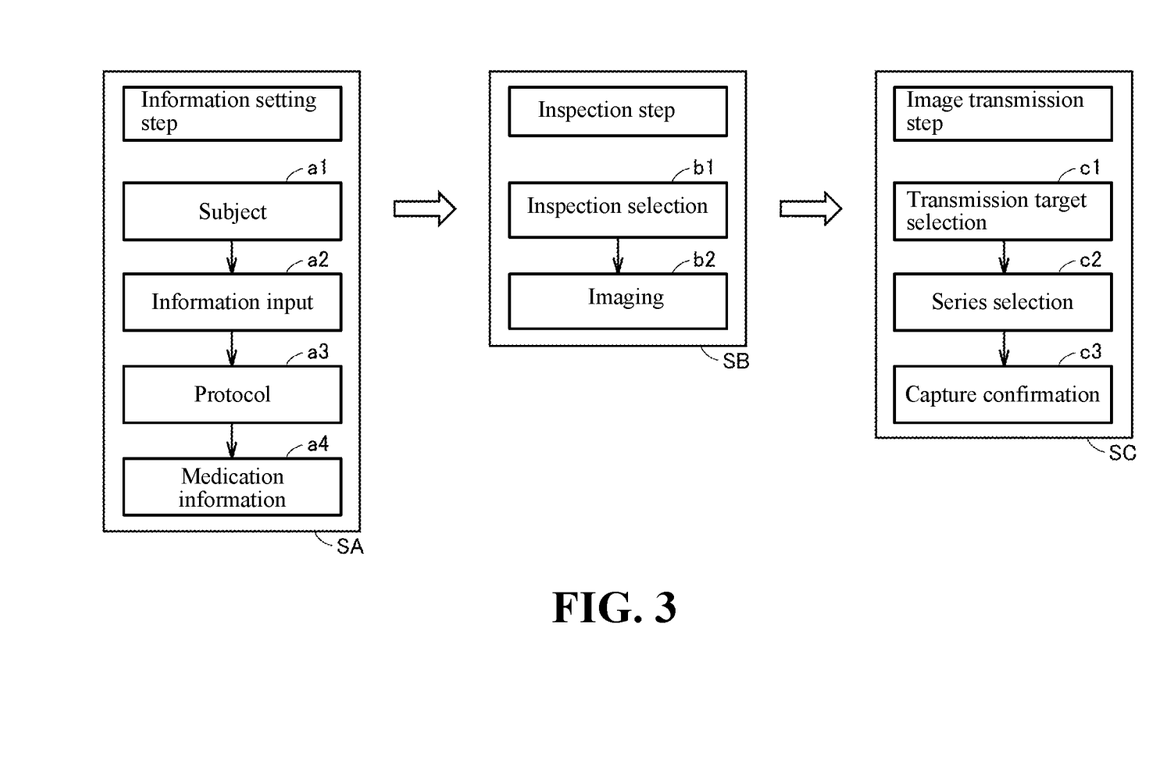
FIG. 3 is a diagram for explaining a flow of generation processing of a PET image.

FIG. 3 is a diagram for explaining the flow of generation processing of the PET image. Referring to FIG. 3, the generation processing of the PET image includes an information setting step SA, an inspection step SB, and an image transmission step SC.

The information setting step SA is a step of setting information required to generate a PET image. The information setting step SA includes a step a1 for selecting a subject, a step a2 for setting the subject information, a step a3 for setting the protocol, and a step a4 for setting the medication information.

In the step a1 for selecting a subject, a subject to be inspected is selected from a list of subjects created in advance. In the step a2 for setting the subject information, the information on the subject selected in the step a1 is set. The information on the subject includes information, such as, e.g., the body height, the body weight, and the blood sugar level of the subject.

In the step a3 for setting a protocol, the inspection condition is set. In the inspection condition, an inspection start time, an inspection site, a collection time of emission data, an image reconstruction condition, etc., are included. In the step a4 for setting the medication information, the information, such as, e.g., a type of a radioactive pharmaceutical administered to the subject and the date and time when the radioactive pharmaceutical was administered, is set.

The information can be set by the operator by operating the operation unit 22. In this embodiment, the operator can set the information by touch-operating the objects displayed on the display screen of the touch panel 20. The information set in the information setting step SA is transmitted from the operation unit 22 to the imaging control unit 16. The imaging control unit 16 stores the transmitted information in the storage unit 18.

The inspection step SB is a step of collecting emission data from the subject M using the information set in the information setting step SA and reconstructing the collected emission data to generate a PET image. The inspection step SB has a step b1 for selecting an inspection and a step b2 for imaging.

In the inspection selection step b1, the inspection site in the subject M is selected. The operator operates the operation unit 22 to select the inspection site of the subject M. In the step b2 of imaging, γ-rays generated from the inspection site of the subject M to which a radiopharmaceutical has been administered are detected by the PET detector 3 and emission data is collected based on the detected γ-rays. By reconstructing the collected emission data, a PET image is generated.

The image transmission step SC is a step of transmitting the PET image generated in the inspection step SB to the server. The image transmission step SC includes a step c1 of selecting a transmission target, a step c2 of selecting a series, and a step c3 of confirming capturing of an image.

In the step c1 of selecting a transmission target, a PET image to be transmitted to a server communicatively connected to the PET apparatus 100 is selected. In the step c2 of selecting a series, a series of PET images to be transmitted to the server is selected. In the step c3 of confirming capturing of an image, the captured PET image is displayed on the display screen of the display unit 24 to confirm whether the PET image has been captured normally. The PET image captured normally is stored in the storage unit 18. The PET image of the transmission target stored in the storage unit 18 is transmitted to the server.

The operator of the PET apparatus 100 sequentially performs the information setting step SA, the inspection step SB, and the image transmission step SC shown in FIG. 3 for one subject M. However, the information to be set in the information setting step SA includes information that cannot be determined until immediately before the inspection, such as, e.g., the body weight of the subject M and the medication information. Therefore, the operator is required to set a lot of information immediately before the inspection, so that there is a concern that it takes time and effort.

In addition, in the inspection step SB, it usually takes a relatively long time of about 5 to 20 minutes to generate a PET image of one subject M. Therefore, in cases where there is a plurality of subjects M, there is a problem that it takes a considerably long time to perform processing for generating PET images for all the subjects.

Figure 4:
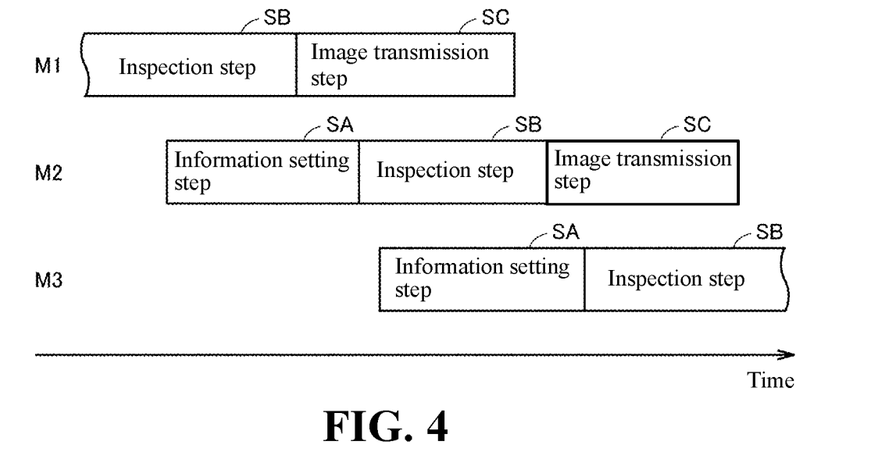
FIG. 4 is a diagram for explaining a flow of processing for generating PET images of a plurality of subjects.

Therefore, conventionally, in the case of generating PET images of a plurality of subjects, the efficiency of work is improved by performing generation processing of PET images of a plurality of subjects in parallel. For example, as shown in FIG. 4, while performing the inspection step SB of one subject M2, an information setting step SA for a subject M3 to be subjected to the next inspection is performed. Or, the image transmission step SC for the subject M1 for which the inspection has already completed is performed. For example, while a PET image in the inspection step SB of the subject M2 is being generated, the information on the subject M3 is input. Alternatively, the PET image of the subject M1 is confirmed and transmitted to the server.

Here, in a conventional PET apparatus, as shown in FIG. 4, during the performance of the inspection step SB of the subject M2, when the information setting step SA of the subject M3 or the image transmission step SC of the subject M1 is performed, a method is adopted in which in the state, in which a captured PET image is displayed on the display screen of the display unit, a setting screen of another step is displayed on the display screen. In this method, it is troublesome if the important information in the inspection step SB cannot be seen, it is configured such that the work can be performed by displaying the setting screen of another step while securing a display region of the captured image. Therefore, there is a concern that the size of the display region for displaying each step becomes small and the transition of the screen becomes complicated. Further, since the screen becomes complicated, there is a concern that an erroneous operation, such as, e.g., erroneous information inputs and information input omissions, may occur.

Further, in a conventional PET apparatus, in many cases, it allows operator's own customization, and there are some cases in which setting screens for procedures other than standard works, such as, e.g., setting screens for respective steps, an avoidance means (display of an error or a warning) in the case of erroneous operations, and a recovery means from erroneous operations, are prepared. Therefore, a lot of objects and information are displayed on the display screen, resulting in a complicated GUI. As a result, the instruction manual of a PET apparatus tends to become thick, and there is no description about the flow of the custom routine work of the operator in the thick and exhaustive instruction manual. This causes the necessity of generating an operation procedure manual for each operator, and there is a concern that the operation procedure will become complicated.

Further, in a conventional PET apparatus, a message for drawing an operator's attention is generally displayed using a pop-up window on the display screen of the display unit. Depending on the timing at which this pop-up window is displayed, there is a concern that operations are interrupted or setting screens become invisible. Also, in order to delete the pop-up window, the operator needs to remember what kind of message was displayed.

Therefore, in this embodiment, a PET apparatus is provided in which an operator can efficiently work with a simple operation.

Figure 5:
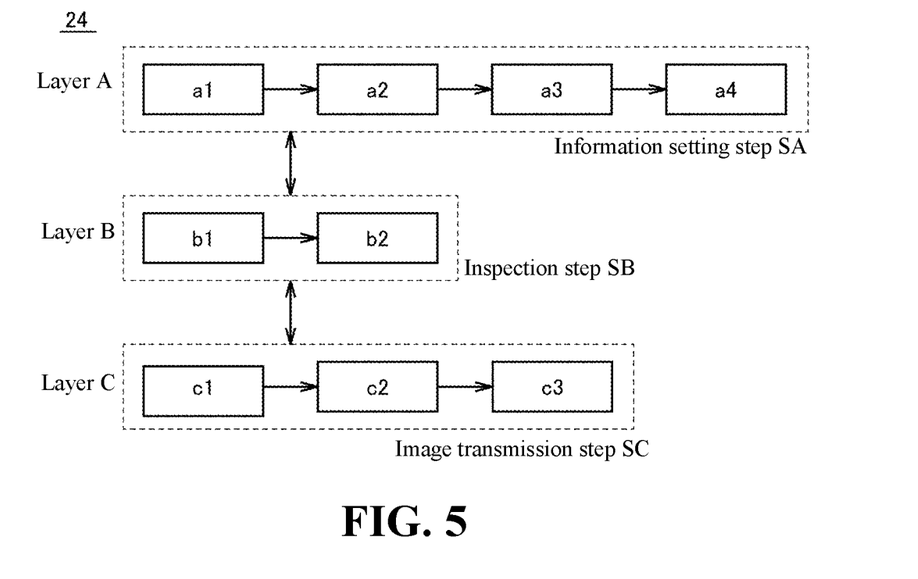
FIG. 5 is a diagram schematically showing a configuration example of a display screen of a display unit.

Specifically, in the PET apparatus 100 according to this embodiment, the display unit 24 is configured to display layers for displaying the respective setting screens of the information setting step SA, the inspection step SB, and the image transmission step SC in a superimposed manner. FIG. 5 is a diagram schematically showing a configuration example of the display screen of the display unit 24.

Referring to FIG. 5, the layer A configures a setting screen for performing the information setting step SA. The layer B configures a setting screen for performing the inspection step SB. The layer C configures a setting screen for performing the image transmission step SC.

The display unit 24 displays these three layers A to C on the display screen in a superimposed manner. The display unit 24 can switch the layer to be displayed in the uppermost layer in accordance with the input operation of the operator on the operation unit 22.

Note that only the layer displayed in the uppermost layer can receive the setting of the operator on the setting screen. As described later, in the setting screen displayed in the layer, as a method of setting a plurality of pieces of information in each step, setting in a wizard format is applied.

Figure 6:
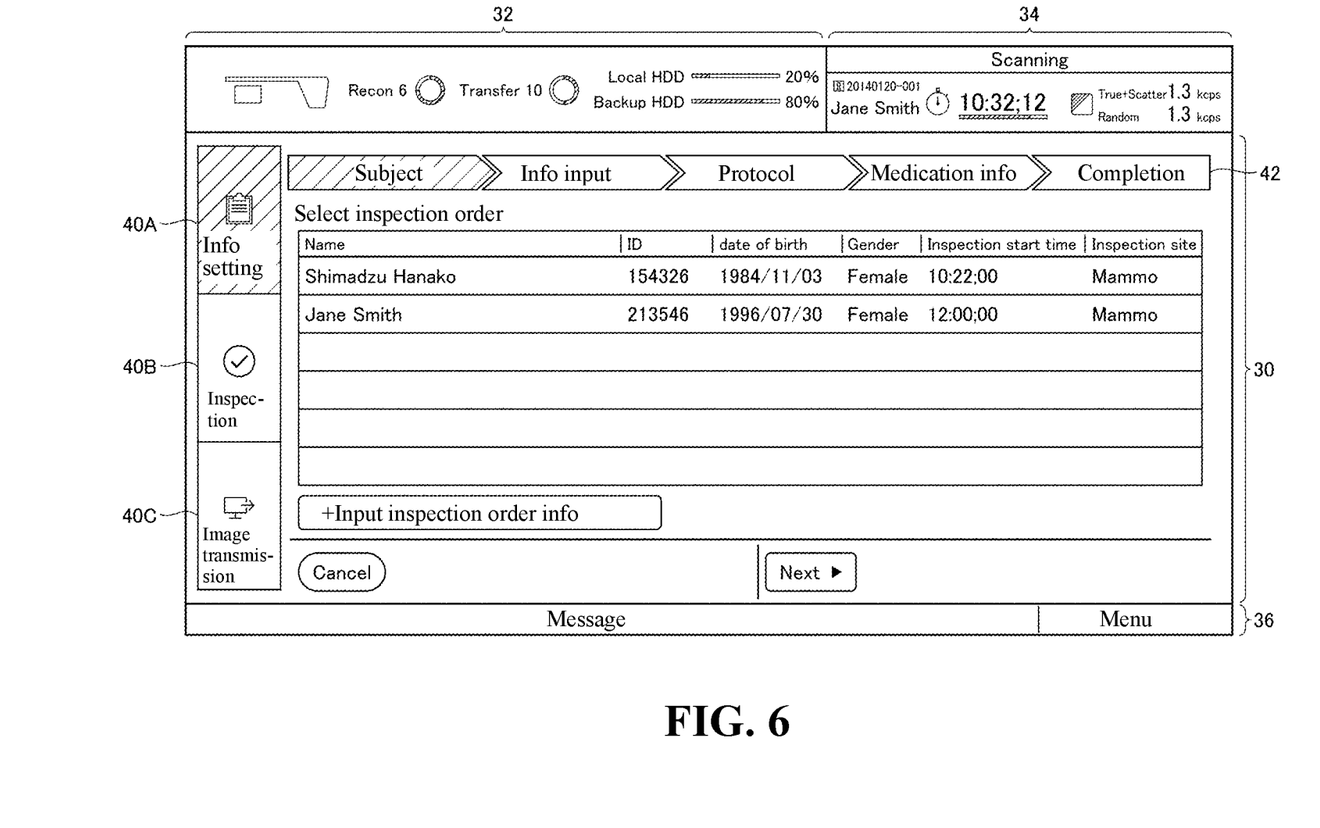
FIG. 6 is a diagram showing a display example of a display screen of a display unit.

FIG. 6 is a view showing a display example of the display screen of the display unit 24. Referring to FIG. 6, the display screen of the display unit 24 has a plurality of display regions 30, 32, 34, and 36.

The display region 30 is a region for displaying each setting screen of the information setting step SA, the inspection step SB, and the image transmission step SC. At the end portion of the display region 30, three tabs 40A, 40B, and 40C are provided. The tabs 40A, 40B, and 40C each constitute an object for selecting a layer to be displayed in the uppermost layer between the three layers A to C described above. In the example of FIG. 6, the step name of the corresponding layer is described in each tab. When the operator performs a touch operation of the tab 40A, the layer A is displayed in the uppermost layer, when the operator performs a touch operation of the tab 40B, the layer B is displayed in the uppermost layer, and when the operator performs a touch operation of the tab 40C, the layer C is displayed in the uppermost layer. The tabs 40A to 40C each correspond to an example of an object for selecting an uppermost layer.

The display example of FIG. 6 shows a display screen in a state in which the tab 40A is touch-operated. When the layer A is made in a selected state by performing a touch operation of the tab 40A, the setting screen of the information setting step SA is displayed in the display region 30.

The setting screen receives setting of information based on the operation by the operator received by the operation unit 22. In this embodiment, the setting screen displays a wizard screen for allowing the operator to set information in an interactive format. The wizard screen is a screen for sequentially setting a plurality of pieces of information in the wizard format.

In the example of FIG. 6, a display bar 42 for displaying the progress of the information setting step SA is arranged in the display region 30. The display bar 42 is divided into five segments. Four segments out of the five segments correspond to the step a1 for selecting a subject, the step a2 for setting subject information, the step a3 for setting a protocol, and the step a4 for setting medication information. The remaining segment shows that the information setting step SA has been completed. Further, in the display region 30, a button ("Next" in the figure) for transitioning to the next wizard screen and a button (not shown) for returning to the previous wizard screen are arranged.

The imaging control unit 16 sequentially receives the settings of a plurality of pieces of information in the information setting step SA based on the operation input to the wizard screen in the display region 30. As described above, in the setting in the wizard format, the operator can easily perform the settings of a plurality of pieces of information by advancing the operations in the interactive format.

Note that, in the example of FIG. 6, the layers B and C corresponding to the tabs 40B and 40C are in a non-selected state, and therefore they are arranged under the layer A and do not appear on the display screen. When the operator performs a touch operation on the tab 40B in this state, the layer B becomes in a selected state, and the display region 30 is switched from the setting screen of the information setting step SA to the setting screen of the inspection step SB. On the other hand, when the tab 40C is touch-operated, the layer C becomes in a selected state, and the display region 30 is switched from the setting screen of the information setting step SA to the setting screen of the image transmission step SC.

Around the display region 30, display regions 32, 34, and 36 are arranged. The display region 32 is a region for displaying the status information of the PET apparatus 100. The status information includes information, such as, e.g., the number of PET images reconstructed by the PET apparatus 100, the number of PET images transmitted to the server, and the usage status (capacity used) of the storage unit 18.

The display region 34 is a region for displaying the information in the middle to the inspection by the PET apparatus 100. The information in the middle of the inspection includes the information on, for example, the subject in the middle of the inspection and the inspection time.

The display region 36 is a region for displaying a message to the operator. The message includes a message (such as, e.g., an error message and a warning) for alerting the operator.

Note that, as for the display regions 32, 34, and 36, they are configured such that even if the setting screen displayed on the display region 30 changes, the display content does not change. According to this, the operator can perform the setting of the information on the setting screen and the switching of the setting screen while confirming the status information of the PET apparatus 100, the information in the middle of the inspection, and the message.

In the example of FIG. 6, in the display region 36, a menu for performing a custom setting for the setting screen to be displayed in the display region 30 is further arranged. Note that the position and the layout of each of the display regions 30, 32, 34, and 36 in the display screen are not limited to the display example of FIG. 6, and various modifications can be made.

Next, setting of information in the information setting step SA, the inspection step SB, and the image transmission step SC will be described. As described above, the setting in a wizard format is applied to the setting of information in each step.

(Information Setting Step SA)

Figure 7:
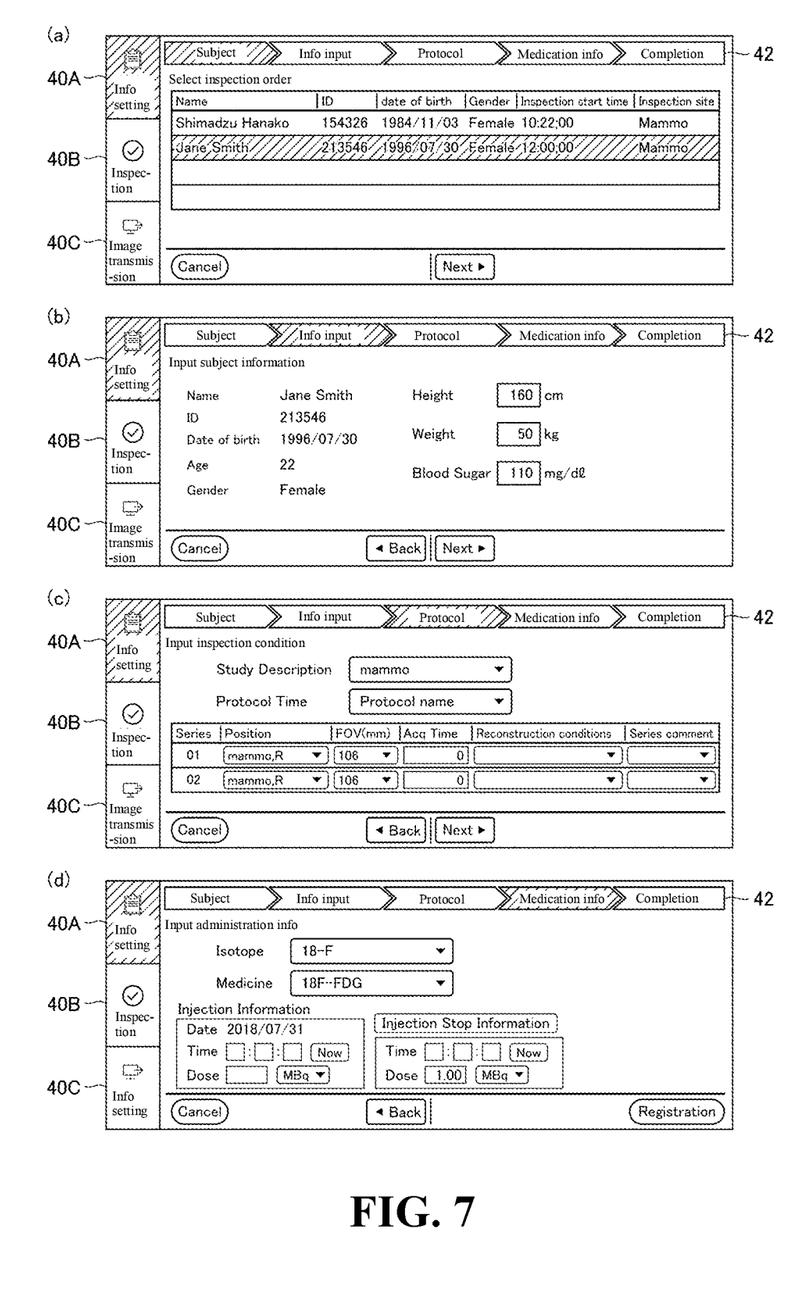
FIG. 7 is a view showing a display example of a setting screen for performing an information setting step.

FIG. 7 is a diagram showing display examples of the setting screen for performing the information setting step SA. FIG. 7 shows the display region 30 extracted from the display screen of the display unit 24.

As shown in FIG. 3, the information setting step SA is a step of setting information required to generate a PET image, and includes a step a1 for selecting a subject, a step a2 for setting the subject information, a step a3 for setting the protocol, and a step a4 for setting the medication information.

In the information setting step SA, first, a wizard screen for performing the step a1 for selecting a subject shown in (a) of FIG. 7 is displayed. In the display example of (a) of FIG. 7, a list of subjects is displayed on the wizard screen. When the operation unit 22 receives an operation of selecting a subject to be inspected from the list, a wizard screen for performing the step a2 for setting the subject information shown in (b) of FIG. 7 is displayed on the display unit 24.

In the display example shown in (b) of FIG. 7, in addition to the name, the ID, the date of birth, the age and gender of the subject, objects for setting the body height, the body weight, and the blood sugar level, are displayed on the wizard screen. When the operation unit 22 receives operations of setting the body height, the body weight, and the blood sugar level, a wizard screen for performing the step a3 for setting the protocol shown in (c) of FIG. 7 is displayed on the display unit 24.

In the display example shown in (c) of FIG. 7, objects for setting an inspection site, an inspection time, an image reconstruction condition, etc., are displayed as inspection conditions on the wizard screen. When the operation unit 22 receives operations of setting these inspection conditions, a wizard screen for performing the step a4 for setting the medication information shown in (d) of FIG. 7 is displayed on the display unit 24.

In the display example shown in (d) of FIG. 7, objects for setting the type of the radioactive pharmaceutical administered to the subject, the date and time when the radioactive pharmaceutical was administered, and the like are displayed on the wizard screen. When the operation unit 22 receives the operation of setting the medication information, the display unit 24 notifies the operator that the information setting step SA has been completed by using the display bar 42.

(Inspection Step SB)

Figure 8:
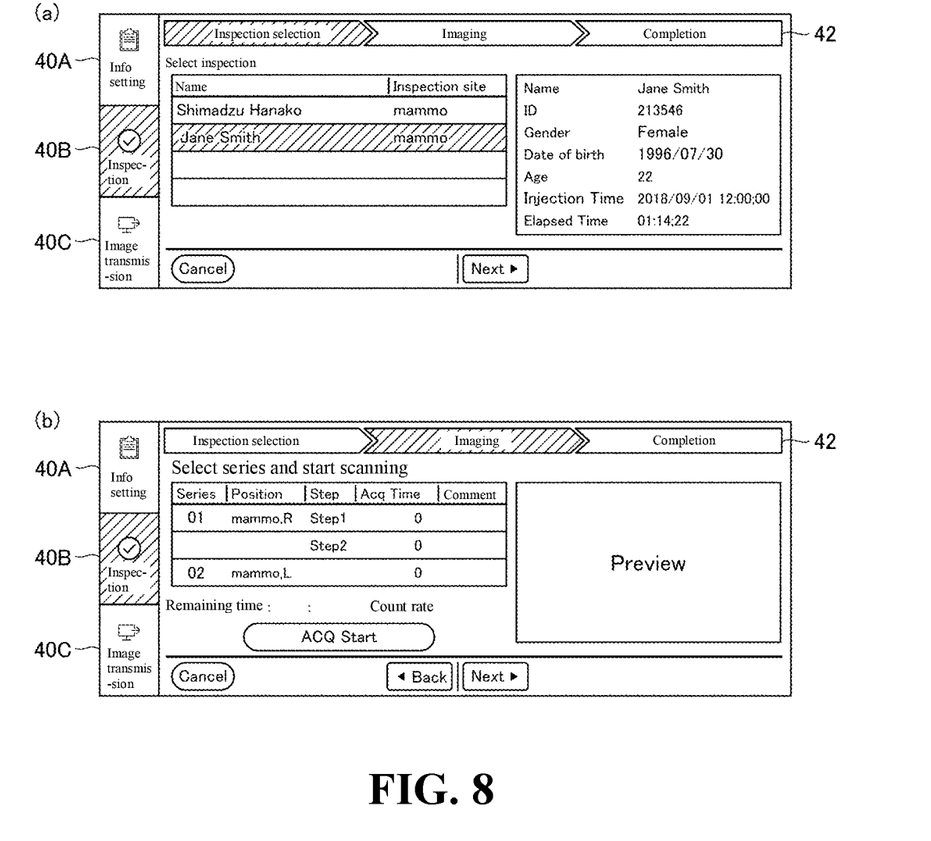
FIG. 8 is a view showing a display example of a setting screen for performing an inspection step.

FIG. 8 is a diagram showing a display example of a setting screen for performing the inspection step SB. Similar to FIG. 7, FIG. 8 shows the display region 30 extracted from the display screen of the display unit 24.

As shown in FIG. 3, the inspection step SB is a step of collecting emission data from the subject M using the information set in the information setting step SA and generating a PET image by reconstructing the collected emission data, and includes a step b1 of selecting an inspection and a step b2 of imaging.

In the inspection step SB, first, a wizard screen for performing the inspection selection step b1 shown in (a) of FIG. 8 is displayed. In the display example of (a) of FIG. 8, a list showing subjects and their inspection sites is displayed on the wizard screen. When the operation unit 22 receives an operation of selecting an inspection target from this list, a wizard screen for performing the imaging step b2 shown in (b) of FIG. 8 is displayed on the display unit 24.

In the display example shown in (b) of FIG. 8, an object for selecting a series of inspections and an object for instructing the start of inspection are displayed. When a series of inspection is selected and the operation unit 22 receives an operation for instructing the start of inspection, the PET apparatus 100 starts collecting emission data according to the inspection condition set in the inspection step SB, and reconstructs a PET image based on the collected emission data. Note that the wizard screen in (b) of FIG. 8 is provided with a preview screen for displaying a reconstructed PET image. The reconstructed PET image is sent to the display unit 24 of the touch panel 20.

(Image Transmission Step SC)

Figure 9:
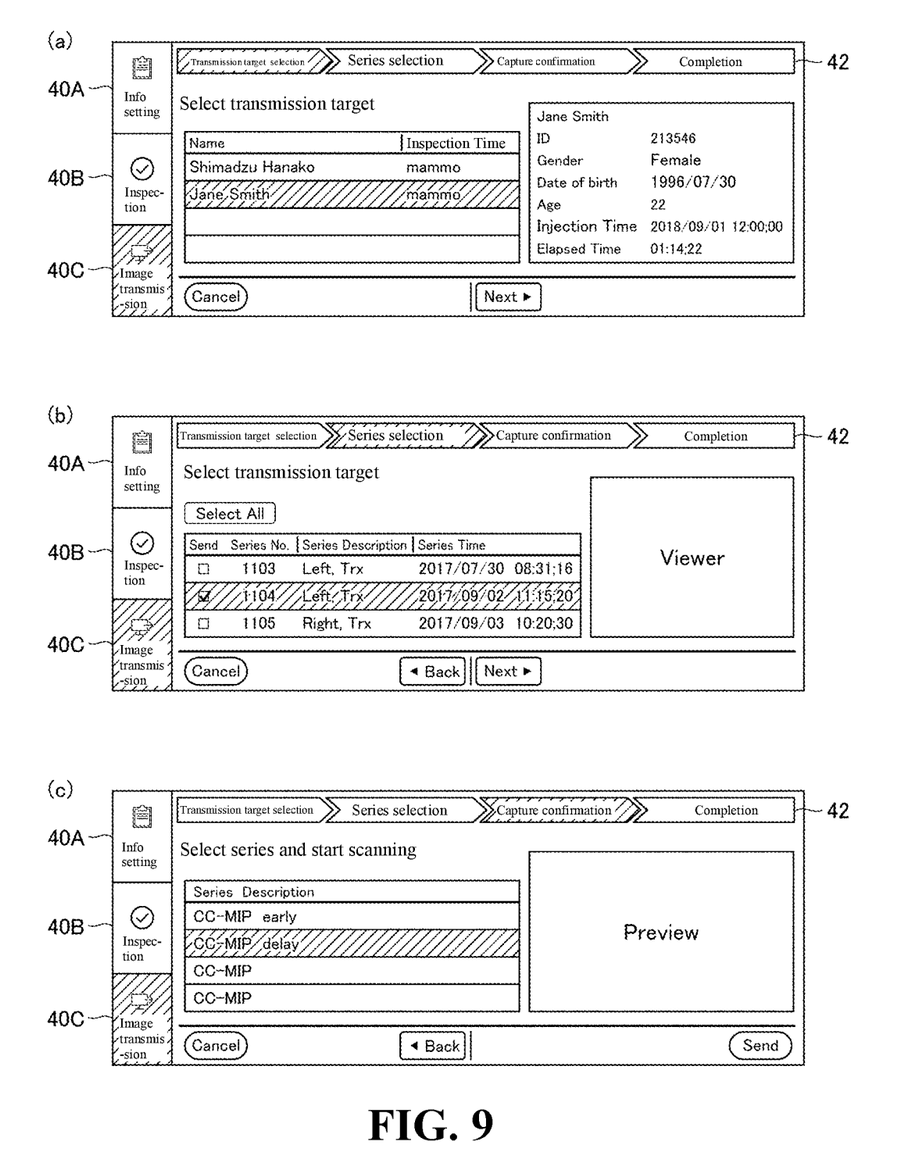
FIG. 9 is a view showing a display example of a setting screen for performing an image transmission step.

FIG. 9 is a diagram showing a display example of the setting screen for performing the image transmission step SC. Similar to FIG. 7 and FIG. 8, FIG. 9 shows the display region 30 extracted from the display screen of the display unit 24.

As shown in FIG. 3, the image transmission step SC is a step of transmitting the PET image generated in the inspection step SB to a server, and includes a step c1 of selecting a transmission target, a step c2 of selecting a series, and a step c3 of selecting a captured image.

In the image transmission step SC, first, a wizard screen for performing the step c1 for selecting a transmission target shown in (a) of FIG. 9 is displayed. In the display example of (a) of FIG. 9, in the wizard screen, a list showing the subject for which the inspection has been completed and the inspection site is displayed. When the operation unit 22 receives an operation of selecting a transmission target from the list, on the display unit 24, a wizard screen for executing the step c2 of selecting a series shown in (b) of FIG. 9 is displayed.

In the display example shown in (b) of FIG. 9, a list of series for which the inspection has been completed for the subject and the inspection site selected as the transmission target is displayed. When the operation unit 22 receives an operation of selecting a series of transmission targets from this list, on the display unit 24, a wizard screen for performing the step c2 for confirming the capturing of an image shown in (c) of FIG. 9 is displayed.

In the display example shown in (b) of FIG. 9, the wizard screen is provided with a preview screen for displaying a captured PET image for the series of the transmission target. The operator looks at the captured image displayed on the preview screen and confirms whether the PET image has been captured normally. When it is confirmed that the image has been normally captured, the operator stores the PET image in the storage unit 18. The PET image of the transmission target stored in the storage unit 18 is transmitted to the server.

Next, the flow of processing in the case of generating PET images of a plurality of subjects using the PET apparatus 100 according to this embodiment will be described.

In the following description, it is assumed that generation processing of PET images of two subjects M1 and M2 is performed in parallel. For example, it is assumed that while the information setting step SA is being performed for the subject M1, the image transmission step SC is performed for another subject M2.

Figure 10:
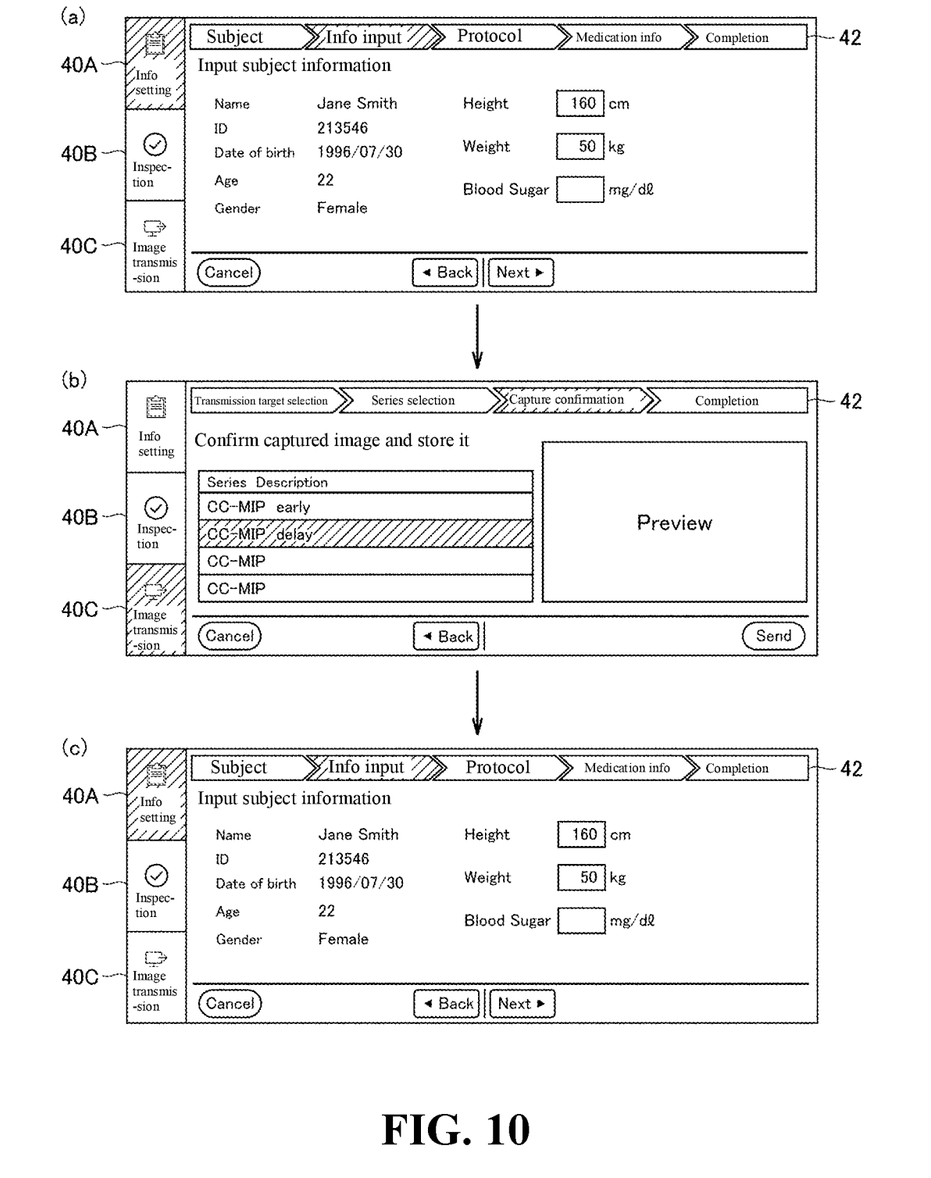
FIG. 10 is a view showing a display example of a display screen of a display unit.

FIG. 10 is a view showing a display example of the display screen of the display unit 24. FIG. 10 shows the display region 30 extracted from the display screen of the display unit 24.

As shown in (a) of FIG. 10, when the operator performs a tap operation on a tab 40A to set a layer A in a selected state, in the display region 30 of the display unit 24, the setting screen of the information setting step SA for the subject M1 (in FIG. 10, Jane Smith) is displayed. As described in FIG. 7, on the setting screen of the information setting step SA, a wizard screen for setting a plurality of pieces of information in the wizard format is displayed. In the display example of (a) of FIG. 10, on the display region 30, a wizard screen for performing the step a2 for setting the subject information is displayed. The wizard screen receives the setting of the information of the subject M1 by the operator.

At this time, when the operator performs a touch operation on the tab 40C to set the layer C in a selected state, as shown in (b) of FIG. 10, in the display region 30, the setting screen of the information setting step SA for the subject M1 is switched to the setting screen of the image transmission step SC for the subject M2. With this, in the PET apparatus 100, the information setting step SA for the subject M1 is interrupted, and it becomes possible to perform the image transmission step SC for the subject M2.

As described in FIG. 9, on the setting screen of the image transmission step SC, a wizard screen for setting a plurality of pieces of information in the wizard format is displayed. In the display example of (b) of FIG. 10, on the display region 30, a wizard screen for performing the step C3 for confirming the image capturing is displayed. In the preview screen of the wizard screen, the captured PET image of the subject M2 is displayed. The operator confirms whether the captured image has been normally imaged, and stores the captured image in the storage unit 18 when it is confirmed that the capture image has been normally captured.

After performing the image transmission step SC for the subject M2, the operator can resume the interrupted information setting step SA for the subject M1. Specifically, the operator performs a touch operation on the tab 40A to make the layer A in a selected state. As a result, in the display region 30, the setting screen of the image transmission step SC for the subject M2 is switched to the setting screen of the information setting step SA for the subject M1.

At this time, as shown in (c) of FIG. 10, on the setting screen of the information setting step SA, the wizard screen displayed at the time of switching to the setting screen of the image transmission step SC is displayed again. The wizard screen of (c) of FIG. 10 is the same as the wizard screen of (a) of FIG. 10. That is, the contents displayed at the time of switching the setting screen are held as they are in the wizard screen. Therefore, the operator can resume the information setting step SA for the subject M1 from the suspended state.

[Functions and Effects]

Hereinafter, the functions and effects exerted by the medical image diagnostic apparatus according to this embodiment will be described.

In the medical image diagnostic apparatus according to this embodiment, the process of generating a medical image of a subject is divided into a plurality of steps, and a plurality of setting screens corresponding to the plurality of steps is displayed on the display screen of the display unit 24 in a superimposed manner. In the display screen of the display unit 24, the setting screen of the uppermost layer is switched according to the operation of the operator of the medical image diagnostic apparatus.

By configuring as described above, when generating medical images of a plurality of subjects using the medical image diagnostic apparatus, while performing one step for one subject, when another step for another subject is performed, the operator can perform two steps in parallel by switching the setting screen of the uppermost layer of the display screen. According to this, when the setting screen of one step is being displayed, since the setting screen of another step is in a non-displayed state, it is clear to the operator which step is currently being performed. Further, compared with the mode in which the two setting screens corresponding to the two steps are displayed side by side on the display screen, the respective setting screens can be prevented from being miniaturized and complicated. As a result, it is possible to reduce the possibility that the operator performs erroneous operations.

Further, in the medical image diagnostic apparatus according to this embodiment, each of the plurality of setting screens is configured to display a plurality of wizard screens for sequentially inputting the plurality of pieces of information to be set in the corresponding step in the wizard format. By setting as described above, the number of objects displayed on each setting screen can be reduced, so the setting screen can be simplified and the operability can be improved. Further, since the operator can set a plurality of pieces of information by performing the operation in the interactive format, the setting of the plurality of pieces of information can be simplified.

In the medical image diagnostic apparatus according to this embodiment, furthermore, in cases where the operation unit 22 receives an operation for switching the setting screen of the uppermost layer, at the time when the operation is received, the setting screen of the uppermost layer is switched while holding the wizard screen displayed on the setting screen of the uppermost layer. According to this, in the case of performing a plurality of steps in parallel, the setting screen of the uppermost layer can be switched between a plurality of setting screens while retaining the information input for the setting screen in each step. Therefore, when the setting screen of the uppermost layer is switched, it is possible to avoid duplication of effort that information is set from the beginning in the setting screen after the switching. As a result, the work efficiency in the process of generating medical images of a plurality of subjects can be improved.

Further, in the medical image diagnostic apparatus according to this embodiment, the display screen of the display unit 24 is provided with, separately from the display region for displaying the setting screen, regions for displaying the status information of the medical image diagnostic apparatus, the information in the middle of the inspection, a message to an operator, and the like. According to this, the operator can always check the progress of the inspection and the operating status of the medical image diagnostic apparatus while setting the information on the setting screen or while confirming the capturing of a medical image. Further, when setting information on the setting screen, even if a message, such as, e.g., an error message and a warning message, occurs, the message is displayed in the display region other than the setting screen, so the setting screen is not disturbed.

Furthermore, as shown in FIG. 5, in the display screen of the display unit 24, the setting screen for customizing the setting in each step is organized into a menu screen and displayed in a display region other than the setting screen. According to this, the operation in the wizard screen can be minimized. Further, when setting is customized from the menu screen, it may be configured such that the setting is reflected in the order of the wizard format set in advance. According to this, even if there are different settings or operations for each operator, they will be reflected in the order of the work procedure, which can compensate for the demerits of the wizard format.

In the PET apparatus 100 according to the above-described embodiment, the configuration is described in which the process of generating a PET image is divided into three steps (information setting step, inspection step, and image transmission step), and three setting screens corresponding to the respective three steps are displayed. However, the process of generating a PET image may be divided into two or four or more steps. Further, in the setting of information in the wizard format in each step, the configuration and the number of wizard screens to be displayed are not limited to the configuration of the embodiment, and various modifications may be made.

In the above-described embodiment, the PET apparatus for diagnosing a breast of a subject is exemplified, but the medical image diagnostic apparatus according to the present invention is not limited to a PET apparatus, and may be applied to an apparatus for generating a medical image of a subject.

It should be understood that the embodiments disclosed here are examples in all respects and are not restrictive. The scope of the present invention is shown by claims rather than the above descriptions, and is intended to include all changes within the meaning of equivalent and the scope of claims.

DESCRIPTION OF REFERENCE SYMBOLS

1 gantry
2 opening portion
3 PET detector
4 support portion
5 drive unit
6 drive control unit
7 emission data collection unit
10 console
12 absorption correction unit
14 PET reconstruction unit
16 imaging control unit,
18 storage unit
20 touch panel
22 operation unit
24 display unit
30, 32, 34, 36 display region
40A, 40B, 40C tab
42 display bar
100 PET apparatus
M, M1 to M3 subject

The invention claimed is:

1. A medical image diagnostic apparatus configured to generate a medical image based on data collected from a subject when an operator sequentially performs a plurality of steps, the medical image diagnostic apparatus comprising:
a display unit including a display screen;
an input device configured to receive an operation of the operator to the display screen; and
a processor configured to control the display unit based on the operation received by the input device,
wherein the display unit is configured to:
display a plurality of setting screens respectively corresponding to the plurality of steps on the display screen in a superimposed manner, and
display a plurality of objects side-by-side with a setting screen of an uppermost layer, the plurality of objects respectively representing the plurality of steps,
wherein, when an operation for selecting one of the plurality of objects is received by the input device, the display unit is configured to display a corresponding setting screen to the selected object as the setting screen of the uppermost layer,
wherein the display unit is further configured to display, in each of the plurality of setting screens, a plurality of wizard screens for sequentially inputting a plurality of pieces of information in a wizard format, the plurality of pieces of information being different between the plurality of setting screens,
wherein the plurality of wizard screens that are displayed in each of the plurality of setting screens includes at least a wizard screen that displays a list of patients for selecting a target patient from the list,
wherein when the input device receives the operation while a first wizard screen in a first setting screen is displayed as the setting screen of the uppermost layer for performing a first step for a first target patient, the processor is further configured to switch the setting screen of the uppermost layer to a second wizard screen in a second setting screen for performing a second step for a second target patient while maintaining the first wizard screen in a state in which information inputted in the first wizard screen is maintained, wherein the second setting screen is modified for performing the second step for a third target patient other than the second target patient by selecting the third target patient from the list of patients included in the second setting screen, and
wherein in response to the input device receiving the operation for selecting the first setting screen for resuming the first step for the first target patient while the second wizard screen is displayed as the setting screen of the uppermost layer, the processor is further configured to switch the setting screen of the uppermost layer to the first wizard screen in which the information inputted is maintained.

2. The medical image diagnostic apparatus as recited in claim 1,
wherein the plurality of setting screens includes:
a first setting screen for setting information on the subject;
a second setting screen for setting information on collection of the data and generation of the medical image; and
a third setting screen for setting information regarding storage of the medical image,
wherein the display unit is configured to display the plurality of wizard screens in each of the first to third setting screens, and
wherein the processor is configured to switch the setting screen of the uppermost layer between the first to third setting screens based on the operation received by the input device and switches the setting screen of the uppermost layer in a state in which the wizard screen displayed on the setting screen of the uppermost layer is held when the input device received the operation.

3. The medical image diagnostic apparatus as recited in claim 1, wherein the display screen of the display unit includes:

a first display region for displaying the setting screen of the uppermost layer; and a second display region arranged side by side with the first display region and configured to display status information of the medical image diagnostic apparatus.

4. The medical image diagnostic apparatus as recited in claim 3, wherein the status information includes at least one of information on a progress of the plurality of steps and information on an operating status of the medical image diagnostic apparatus.

5. The medical image diagnostic apparatus as recited in claim 3, wherein the display screen of the display unit further includes a third display region for displaying a message to the operator.

6. The medical image diagnostic apparatus as recited in claim 3, wherein the first display region displays, together with the wizard screen, a progress of the step corresponding to the setting screen of the uppermost layer.

7. A medical image diagnostic apparatus configured to generate a medical image based on data collected from a subject when an operator sequentially performs a plurality of steps, the medical image diagnostic apparatus comprising:

a display unit including a display screen;

an input device configured to receive an operation of the operator to the display screen; and a processor configured to control the display unit based on the operation received by the input device, wherein the display unit includes a plurality of setting screens corresponding to the plurality of steps, and is configured to display a first setting screen between the plurality of setting screens on the display screen based on the operation received by the input device, wherein the display unit is further configured to display a plurality of objects that the input device receives an operation of selecting the first setting screen, corresponding to the plurality of setting screens, the plurality of objects being displayed side-by-side with the first setting screen and respectively representing the plurality of steps, and display a plurality of wizard screens for sequentially inputting a plurality of pieces of information in a wizard format, in each of the plurality of setting screens, the plurality of pieces of information being different between the plurality of setting screens, wherein the plurality of wizard screens that are displayed in each of the plurality of setting screens includes at least a wizard screen that displays a list of patients for selecting a target patient from the list, wherein when the input device receives the operation while a first wizard screen in a first is displayed as the setting screen of the uppermost layer for performing a first step for a first target patient, the processor is further configured to switch the setting screen of the uppermost layer to a second wizard screen in a second setting screen for performing a second step for a second target patient while maintaining the first wizard screen in a state in which information inputted in the first wizard screen is maintained, wherein the second setting screen is modified for performing the second step for a third target patient other than the second target patient by selecting the third target patient from the list of patients included in the second setting screen, and wherein in response to the input device receiving the operation for selecting the first setting screen for resuming the first step for the first target patient while the second wizard screen is displayed as the setting screen of the uppermost layer, the processor is further configured to switch the setting screen of the uppermost layer to the first wizard screen in which the information inputted is maintained.

* * * * *